(12) United States Patent
Gotfried

(10) Patent No.: US 7,488,328 B2
(45) Date of Patent: Feb. 10, 2009

(54) TARGETING APPARATUS FOR BONE FIXATION DEVICE

(76) Inventor: Yechiel Gotfried, 10, Ben Gurion Avenue, 27000 Kiryat-Bialik (IL)

( * ) Notice: Subject to any disclaimer, the term of this patent is extended or adjusted under 35 U.S.C. 154(b) by 588 days.

(21) Appl. No.: 10/896,125

(22) Filed: Jul. 20, 2004

(65) Prior Publication Data
US 2006/0030859 A1 Feb. 9, 2006

(51) Int. Cl.
*A61B 17/58* (2006.01)
(52) U.S. Cl. .................................................. 606/99
(58) Field of Classification Search .................. 606/62, 606/64, 96, 99, 104
See application file for complete search history.

(56) References Cited

U.S. PATENT DOCUMENTS

| | | | |
|---|---|---|---|
| 3,019,789 A * | 2/1962 | Whitehill et al. ............ 606/148 |
| 4,827,917 A | 5/1989 | Brumfield |
| 5,032,125 A | 7/1991 | Durham et al. |
| 5,066,296 A * | 11/1991 | Chapman et al. ............... 606/64 |
| 5,176,681 A | 1/1993 | Lawes et al. |
| 5,178,621 A | 1/1993 | Cook et al. |
| 5,334,192 A | 8/1994 | Behrens |
| 5,403,321 A | 4/1995 | DiMarco |
| 5,662,652 A * | 9/1997 | Schafer et al. ................ 606/61 |
| 5,728,128 A | 3/1998 | Crickenberger et al. |
| 6,139,550 A * | 10/2000 | Michelson ................... 606/69 |
| 6,183,477 B1 | 2/2001 | Pepper |
| 6,235,031 B1 | 5/2001 | Hodgeman et al. |
| 6,331,179 B1 * | 12/2001 | Freid et al. .................... 606/61 |
| 6,443,954 B1 | 9/2002 | Bramlet et al. |
| 6,656,189 B1 | 12/2003 | Wilson et al. |
| 2002/0151898 A1 | 10/2002 | Sohngen et al. |
| 2002/0156473 A1 | 10/2002 | Bramlet et al. |
| 2006/0100626 A1 * | 5/2006 | Rathbun et al. ............... 606/69 |

FOREIGN PATENT DOCUMENTS

| | | |
|---|---|---|
| EP | 0 257 118 B1 | 6/1990 |
| EP | 0 521 600 B1 | 6/1996 |
| WO | WO 02/083015 A1 | 10/2002 |

* cited by examiner

*Primary Examiner*—Eduardo C Robert
*Assistant Examiner*—David Comstock
(74) *Attorney, Agent, or Firm*—Frishauf, Holtz, Goodman & Chick, P.C.

(57) ABSTRACT

Apparatus is provided for use with a bone fixation device. The apparatus includes a targeting device, adapted to aid in fixation of the bone fixation device to a bone of a subject. The targeting device includes a coupling element, adapted to couple the targeting device to the bone fixation device. The targeting device additionally includes a coupling assembly, adapted to hold the coupling element and to inhibit the coupling element from exiting the coupling assembly even when the coupling element is not coupled to the bone fixation device.

29 Claims, 5 Drawing Sheets

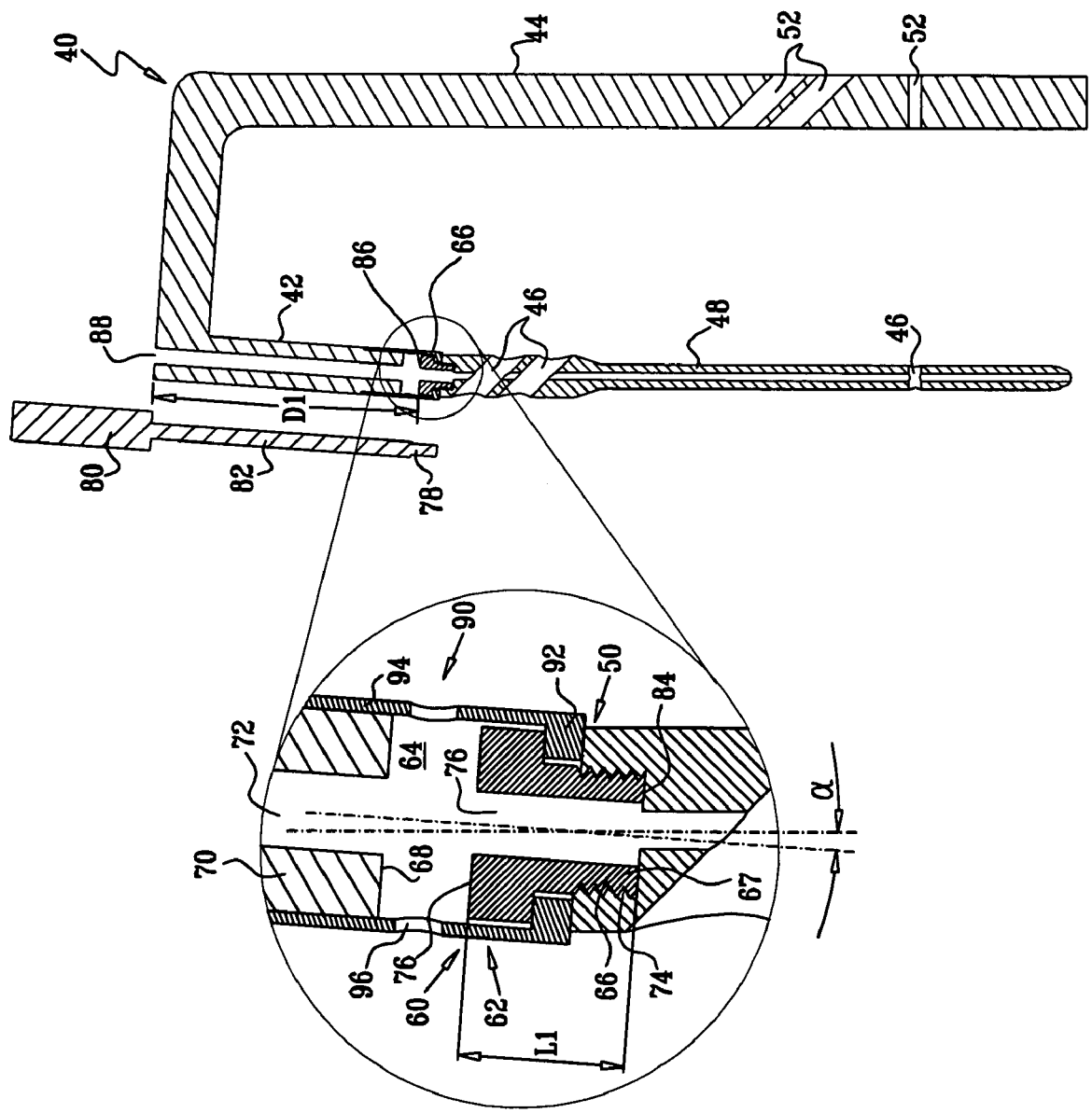

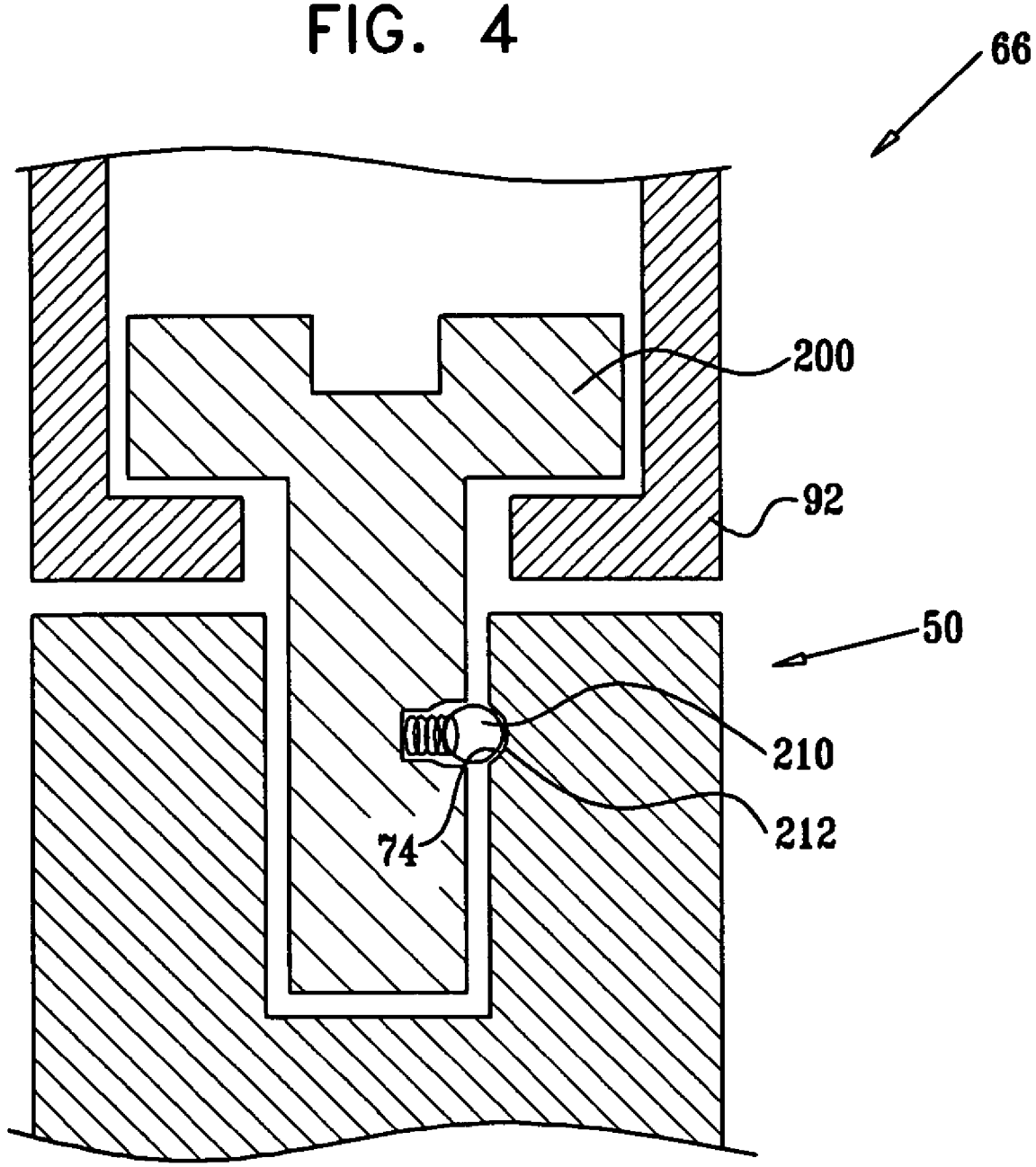

TARGETING APPARATUS FOR BONE FIXATION DEVICE

FIELD OF THE INVENTION

The present invention relates generally to implantable devices for treating bone fractures, and specifically to a targeting device for implanting a bone fixation device.

BACKGROUND OF THE INVENTION

Intramedullary (IM) nails are implantable devices used to stabilize fractures and allow for bone healing. IM nails are inserted into the medullary canal of the long bones of the extremities, e.g., the femur, tibia, or humerus. Currently-used IM nails have a head region that generally includes at least one hole, transverse to the longitudinal axis of the nail, for receiving anchoring means, such as a screw, to secure the nail within the medullary canal of the bone.

Reference is made to FIG. 1, which is a schematic illustration of a targeting device 10, as known in the prior art. Targeting device 10 is used to align one or more IM anchoring screws (not shown) with transverse holes 12 of an IM nail 14, by inserting the IM anchoring screws and/or a drill bit through corresponding aligned transverse holes 16 in targeting device 10. IM nail 14 is inserted into a medullary canal, and targeting device 10 is attached to a proximal end 18 of the IM nail, typically by a screw 20. Screw 20 is inserted into a screw hole 22 at the time of attachment of targeting device 10 to IM nail 14, such that a proximal end 24 of the screw is readily accessible from outside the screw hole. A conventional screwdriver 26 is typically used to tighten screw 20 into IM nail 14.

It is typical to take radiographic images, such as X-ray or fluoroscopic images, during the IM nail implantation procedure, in order to check the alignment of the IM anchoring screws before drilling through the bone. At least a portion of targeting device 10 typically comprises a radiolucent material, such as carbon, in order to minimize the interference of the targeting device with the radiographic images. Screw 20, however, typically comprises a radiopaque metal. Although metal interferes with the radiographic imaging, its use is considered necessary to provide strong coupling between targeting device 10 and IM nail 14.

U.S. Pat. No. 6,183,477 to Pepper, which is incorporated herein by reference, describes an attachment tool for attaching a drill guide to a medical implant such as an intramedullary nail. The attachment tool includes a first end and a housing. The first end includes a first opening that allows a fastener to pass through and thread into the implant, thereby attaching the tool. The housing includes a second opening whose longitudinal axis is preferably offset from the longitudinal axis of the first opening. The housing also includes a guide surface with a groove for directing a driving tool to the second opening. The driving tool is inserted through the second opening to drive the fastener. The driving tool can be inserted and removed during the procedure. The housing also includes a plurality of holes that can be used as drill guide holes or to attach separate drill guides or other orthopedic devices.

U.S. Pat. No. 5,334,192 to Behrens, which is incorporated herein by reference, describes a targeting device for attachment to an implant for treating fractures, such as an intramedullary nail. The targeting device has a targeting arm that extends substantially parallel to the nail, and has a plurality of targeting bores for receiving a drill sleeve, such targeting bores extending at different angles with respect to the axis of the targeting arm.

European Patent EP 0 257 118 B1 to Grosse et al., which is incorporated herein by reference, describes an intramedullary femur nail, and a femur neck screw retained and guided in a transverse throughbore of the femur nail.

U.S. Pat. No. 5,176,681 to Lawes et al., which is incorporated herein by reference, describes an intramedullary intertrochanteric fracture fixation appliance comprising an intramedullary rod having an angulated opening to receive a femoral neck screw. The rod has a co-axial bore extending into the angulated opening, and anti-rotation means located in the bore to selectively prevent rotation of the neck screw in the rod. The open end of the bore is provided with means to positively locate a removable fitting device on the proximal end of the rod, and so that the anti-rotation means can be operated with the fitting device in position.

U.S. Pat. No. 6,656,189 to Wilson et al., which is incorporated herein by reference, describes a radiolucent aiming guide for locating and drilling through the holes in the distal end of an implanted intramedullary nail. The aiming guide comprises an elongate handle constructed substantially of a radiolucent material, which does not cast a strong image on a monitor when exposed to radiation. The radiolucent handle is used in conjunction with a protection sleeve, trocar, drill sleeve, and drill bit, which are used to locate and drill through the hole in the nail. Radiopaque components in the distal end of the protection sleeve, trocar, and drill bit are used to align the drill over the nail hole. A pair of radiopaque pins, located within the handle and lying parallel to its longitudinal axis, aid in ensuring the proper rotational alignment of the aiming guide over the nail hole. The aiming guide may also include a structure to facilitate its alignment over a second hole in the distal end of the intramedullary nail.

U.S. Pat. No. 5,728,128 to Crickenberger et al., which is incorporated herein by reference, describes a femoral neck anteversion guide for use with a femur having a prepared intramedullary canal. The guide includes a radiolucent stem having a distal end for inserting into the prepared intramedullary canal, and a radiopaque angle locator wire embedded within the stem at a known angle for allowing the femoral neck angle and femoral neck anteversion to be determined. The femoral neck anteversion guide preferably includes a handle, which is attached to the radiolucent stem by a radiolucent screw.

U.S. Pat. No. 5,403,321 to DiMarco, which is incorporated herein by reference, describes a radiolucent drill guide for connection to the proximal end portion of an intramedullary nail for aligning a drill with bores of an intramedullary nail when the nail is surgically positioned within an intramedullary canal of a patient. The drill guide includes a handle member of radiolucent material and a guide barrel embedded within the handle. The handle includes an inner generally cylindrical bore and an outer surface that is bonded to closely surround the radiolucent material of the handle member so that the barrel does not rotate freely relative to the handle. The guide barrel includes flanges for preventing relative movement of the barrel in the direction of the central longitudinal axis of the bore of the barrel. A plurality of openings in the handle are at positions spaced away from the barrel for guiding drills when the barrel is affixed to the intramedullary nail so that the drills align with selected openings of the intramedullary nail.

U.S. Pat. No. 5,178,621 to Cook et al., which is incorporated herein by reference, describes a targeting device that includes a radio-transparent handle and a metal snap fit barrel. The radio-transparent handle reduces obstructions in the radiographic image to provide a clearer image to the surgeon for proper placement of the locking screws. The metal snap fit barrel is retained in the handle by an interference fit between the handle and biased keys carried by the barrel.

U.S. Pat. No. 4,827,917 to Brumfield, which is incorporated herein by reference, describes an IM system including a screw and an intramedullary rod. The screw has a threaded portion and a smooth portion, and the rod has a head, stem and a longitudinal bore. There is at least one pair of coaxial holes through the stem, transverse to the longitudinal axis of the rod, for receiving first anchoring means, such as a nail, screw or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw so as to permit the threaded portion of the screw, in use, to engage the femoral head and to allow sliding compression of a femoral neck or intertrochanteric fracture.

U.S. Pat. No. 5,032,125 to Durham et al., which is incorporated herein by reference, describes an IM hip screw that includes an IM rod, a lag screw and a sleeve for slidably receiving the lag screw. The sleeve is received in a passage in the IM rod having an axis positioned at an angle relative to the longitudinal axis of the IM rod such that the axis of the sleeve is directed toward the head of the femur. The IM hip screw is described as permitting sliding compression of selected fractures, particularly intertrochanteric fractures and fractures of the femoral neck.

U.S. Pat. No. 6,443,954 to Bramlet et al., which is incorporated herein by reference, describes an IM system that includes a lag screw assembly extending through a radial bore in an IM nail.

U.S. Pat. No. 6,235,031 to Hodgeman et al., which is incorporated herein by reference, describes an IM system that includes an IM rod, a lag screw, and a lag screw collar.

U.S. Patent Application Publication 2002/0151898 to Sohngen et al., which is incorporated herein by reference, describes an IM nail having a modular configuration, including a nail member having a chamber formed on the proximal end thereof.

U.S. Patent Application Publication 2002/0156473 to Bramlet et al., which is incorporated herein by reference, describes an IM system that includes an IM nail for insertion in the femur. The nail has an axial bore and an intersecting transverse bore. A lag screw is inserted through the transverse bore and turned into the head of the femur. A slotted sleeve is inserted over the lag screw and through the transverse bore with the slots aligned with the axial bore. A sleeve lock is inserted into the axial bore, and has a locking tab which engages the slots in the sleeve preventing rotational and longitudinal movement between the sleeve and the nail. A compression screw is turned into the trailing end of the lag screw and engages the encircling sleeve to provide longitudinal translation between the lag screw and sleeve to apply compressive force across a fracture.

European Patent Application Publication EP 0 521 600 to Lawes, which is incorporated herein by reference, describes an IM system that includes an IM rod having an angulated opening to receive a femoral neck screw having a threaded portion at its distal end, and locking means acting between the neck screw and the wall of the angulated opening to prevent relative rotation between the screw and the rod.

PCT Publication WO 02/083015 to Ferrante et al., which is incorporated herein by reference, describes an orthopedic screw having a screw head, a screw body with a distal tip, a shank with an enlarged diameter at the trailing end and a thread extending radially outward from the shank, and an internal capture surface. The screw is used with an orthopedic implant system, which includes an orthopedic implant and a driver capable of engaging the internal capture of the screw.

SUMMARY OF THE INVENTION

In some embodiments of the present invention, a targeting device, for aiding in the fixation of a bone fixation device to a bone, comprises a coupling assembly for coupling the targeting device to the bone fixation device. The coupling assembly is typically shaped so as to define a retaining arrangement, such as a chamber, pin, or screw assembly, adapted to hold a coupling element, such as a screw, and to prevent the coupling element from exiting the coupling assembly even when the coupling element is not coupled to the bone fixation device. This arrangement enables the coupling element to be shorter than conventional screws used for similar purposes in conventional targeting devices.

Typically, a large portion of the targeting device comprises a radiolucent material, such as carbon, and the coupling element comprises a strong, radiopaque substance, such as a metal, in order to strongly couple the targeting device to the bone fixation device. Because the coupling element is shorter than conventional screws used for similar purposes in conventional targeting devices, the coupling element creates substantially less interference with radiographic images than do such conventional screws.

There is therefore provided, in accordance with an embodiment of the present invention, apparatus for use with a bone fixation device, the apparatus including a targeting device, adapted to aid in fixation of the bone fixation device to a bone of a subject, the targeting device including:

a coupling element, adapted to couple the targeting device to the bone fixation device; and a coupling assembly, adapted to hold the coupling element, and to inhibit the coupling element from exiting the coupling assembly even when the coupling element is not coupled to the bone fixation device.

In an embodiment, the targeting device includes at least one radiolucent material.

In an embodiment, the bone fixation device includes an intramedullary (IM) nail, and the targeting device is adapted to aid in fixation of the IM nail to the bone.

In an embodiment, the bone fixation device includes a plate, and the targeting device is adapted to aid in fixation of the plate to the bone.

In an embodiment, the bone fixation device includes at least one anchoring screw, and the targeting device is shaped so as to define at least one transverse hole therethrough, for aiding in aligning the anchoring screw with the bone fixation device.

In an embodiment, the coupling element includes a screw.

In an embodiment, the coupling element includes a snap-like coupling element.

In an embodiment, the coupling element includes metal.

In an embodiment, the coupling assembly includes at least one radiopaque material.

In an embodiment, the targeting device includes a support element shaped so as to define a support region, which region is adapted to engage the coupling element when the coupling element is coupled to the bone fixation device.

In an embodiment:

the targeting device is shaped to define a longitudinal axis thereof in a portion of the targeting device that couples with the bone fixation device, the bone fixation device is shaped to define a longitudinal axis thereof, and the longitudinal axis of the portion of the targeting device diverges by an angle greater than 2 degrees from the longitudinal axis of the bone fixation device when the coupling element is coupling the targeting device to the bone fixation device.

In an embodiment, the coupling assembly is shaped so as to define a chamber that is adapted to hold the coupling element.

In an embodiment, the chamber is shaped so as to define one or more holes extending between inside the chamber and outside of the targeting device.

In an embodiment, the coupling assembly is shaped so as to define a blocking element that is adapted to inhibit the coupling element from exiting the coupling assembly.

In an embodiment, the coupling element is shaped so as to define a coupling surface at a distal end thereof, and such that a portion of the coupling element that includes the coupling surface is proximal to the blocking element.

In an embodiment, the blocking element is generally cylindrical in shape, and defines a bore through which access is provided to a proximal end of the coupling element.

In an embodiment, the blocking element is shaped so as to define a protrusion from an inner surface of the coupling assembly.

In an embodiment, the coupling element has a proximal end and a distal end, and a distance between the proximal end and the distal end is less than about 15 mm. In an embodiment, the distance is less than about 11 mm. In an embodiment, the distance is less than about 9 mm.

In an embodiment:
the coupling element has a proximal coupling element end,
the targeting device is shaped so as to define an elongated bore having a distal bore end and, at a proximal bore end thereof, a proximal opening,
the coupling assembly is positioned in a vicinity of the distal bore end, and
a distance from the proximal coupling element end to the proximal bore end is greater than about 25 mm, when the coupling element couples the targeting device to the bone fixation device.

In an embodiment, the distance is greater than about 30 mm. In an embodiment, the distance is greater than about 35 mm. In an embodiment, the distance is greater than about 45 mm.

There is further provided, in accordance with an embodiment of the present invention, apparatus for use with a bone fixation device, the apparatus including a targeting device, adapted to aid in fixation of the bone fixation device to a bone of a subject, the targeting device shaped so as to define an elongated bore having a proximal opening at a proximal bore end thereof, and including:
a coupling element having distal and proximal coupling element ends, the coupling element adapted to be insertable into the bore via the proximal opening, and to couple the targeting device to the bone fixation device,
the coupling element and bore shaped such that a coupling element length between the distal coupling element end and the proximal coupling element end is less than about 30 mm, and a bore distance between the proximal coupling element end and the proximal bore end is greater than about 25 mm when the coupling element couples the targeting device to the bone fixation device.

There is still further provided, in accordance with an embodiment of the present invention, a method for coupling a bone fixation device to a targeting device, the targeting device adapted to aid in fixation of the bone fixation device to a bone of a subject, including:

coupling the targeting device to the bone fixation device by means of a coupling assembly that includes a coupling element, the coupling assembly being adapted to hold the coupling element, and to inhibit the coupling element from exiting the coupling assembly even when the coupling element is not coupled to the bone fixation device.

There is yet further provided, in accordance with an embodiment of the present invention, a method for coupling a bone fixation device to a targeting device, the targeting device adapted to aid in fixation of the bone fixation device to a bone of a subject, and the targeting device shaped so as to define an elongated bore having a proximal opening at a proximal bore end thereof, the method including:
inserting, into the bore via the proximal opening, a coupling element having distal and proximal coupling element ends; and
coupling the targeting device to the bone fixation device, using the coupling element,
the coupling element and bore shaped such that a coupling element length between the distal coupling element end and the proximal coupling element end is less than about 30 mm, and a bore distance between the proximal coupling element end and the proximal bore end is greater than about 25 mm when the coupling element couples the targeting device to the bone fixation device.

The present invention will be more fully understood from the following detailed description of embodiments thereof, taken together with the drawings, in which:

BRIEF DESCRIPTION OF THE DRAWINGS

FIG. 2 is a schematic illustration of a targeting device, in accordance with an embodiment of the present invention;

FIG. 4 is a schematic illustration of a snap-like coupling element, in accordance with an embodiment of the present invention.

DETAILED DESCRIPTION OF EMBODIMENTS

Figure 1:
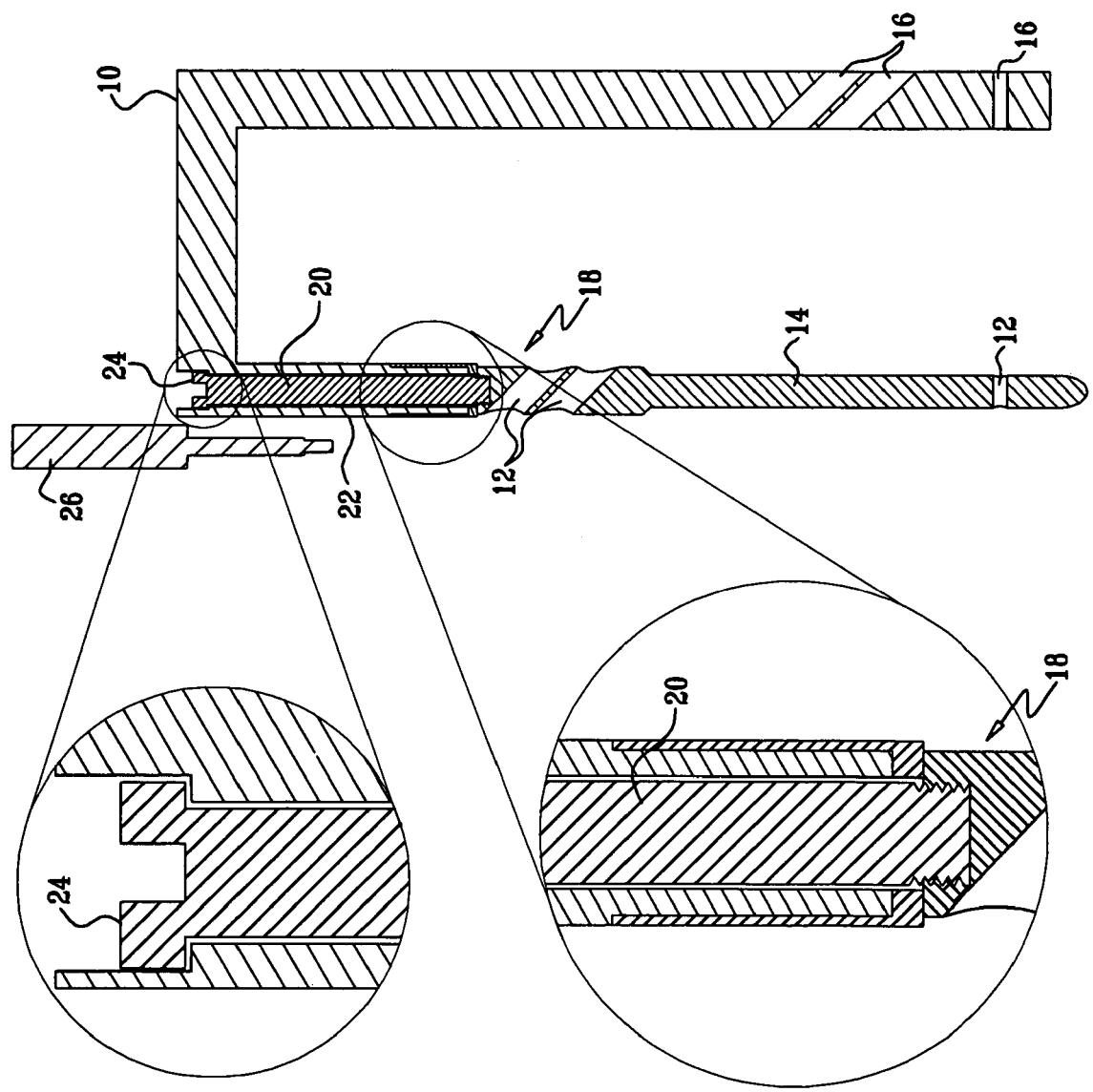
FIG. 1 is a schematic illustration of a targeting device, as is known in the prior art.

FIG. 2 is a schematic illustration of a targeting device 40, in accordance with an embodiment of the present invention. Targeting device 40 typically comprises a coupling portion 42 and an elongated alignment portion 44. For some applications, coupling portion 42 and alignment portion 44 are separate components that are coupled together, either during manufacture or during use, while for other applications, targeting device 40 is formed as an integrated unit that is shaped so as to define coupling portion 42 and alignment portion 44. Typically, a large portion of targeting device 40, e.g., at least about 95%, 90%, or 75% by volume, comprises at least one radiolucent material, such as carbon, carbon fiber composite, or thermoplastic (e.g., Delrin®). For example, substantially all (i.e., at least about 95% by volume) of alignment portion 44 may comprise at least one radiolucent material, and a large portion (i.e., at least about 95%, 90%, or 75% by volume) of alignment portion 44 may comprise at least one radiolucent material.

Targeting device 40 is adapted to aid in the fixation of a bone fixation device 48 to a bone of a subject. Typically, targeting device 40 is used to align one or more anchoring screws (not shown) with transverse holes 46 of bone fixation device 48 after the device has been applied to a fractured bone. For some applications, bone fixation device 48 comprises an intramedullary (IM) nail, which is inserted into a medullary canal of a bone, such as a femur. Alternatively, bone fixation device 48 comprises a plate or other bone fixation device known in the art. Coupling portion 42 of targeting device 40 is attached to a proximal end 50 of bone fixation device 48, and the anchoring screws and/or a drill bit are guided through holes 52 in alignment portion 44, which holes are aligned with corresponding transverse holes 46 of bone fixation device 48.

A distal portion 60 of coupling portion 42 of targeting device 40 comprises a coupling assembly 62 for coupling portion 42 to proximal end 50 of bone fixation device 48. Coupling assembly 62 is typically shaped so as to define a chamber 64 adapted to hold a coupling element 66, such as a screw 67, as shown in FIG. 2. Chamber 64 includes sufficient space to hold coupling element 66 even when the coupling element is not coupled to proximal end 50 of bone fixation device 48. Typically, coupling assembly 62 is configured to prevent coupling element 66 from exiting the coupling assembly even when the coupling element is not coupled to proximal end 50. For example, a distal end 68 of a blocking element 70 may block coupling element 66 from exiting chamber 64. For example, blocking element 70 may be generally cylindrically shaped, and may surround and define a bore 72, as shown in FIG. 2.

A distal end of coupling element 66 is shaped so as to define a coupling surface 74 for securing coupling element 66 to a surface in proximal end 50 of bone fixation device 48. For example, when coupling element 66 comprises screw 67, coupling surface 74 may be shaped so as to define a screw thread. A proximal end of coupling element 66 is shaped so as to define an engagement surface 76, such as an indentation, for receiving a distal end 78 of an activator tool 80. For example, engagement surface 76 and distal end 78 may be hexagonal, square, slotted, or any other shape appropriate for engagement. Activator tool 80 comprises an elongated shaft 82 that is shaped and sized so as to be insertable into bore 72 of coupling portion 42 of targeting device 40.

Figure 3A:
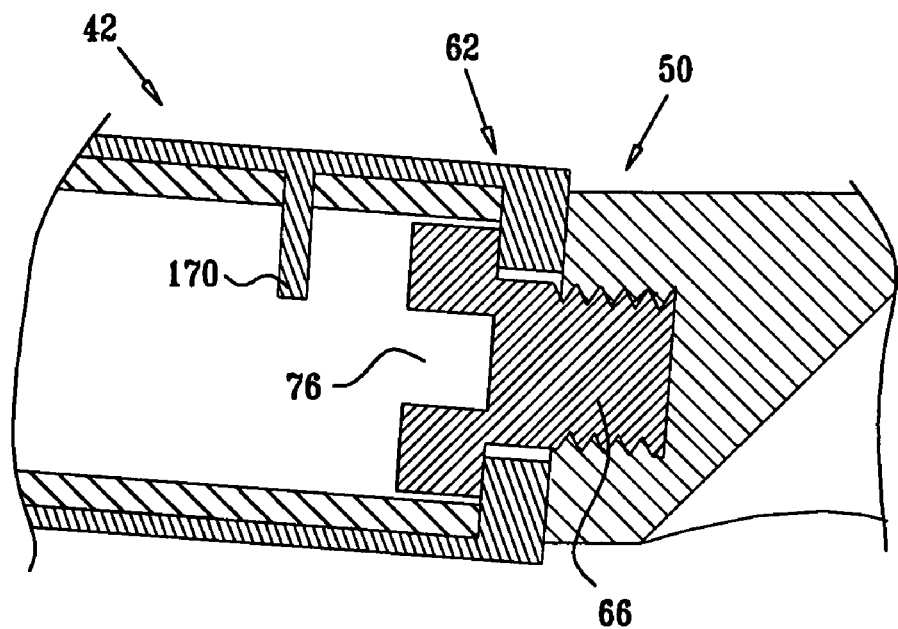
FIGS. 3A and 3B are schematic illustrations of configurations of a coupling assembly, in accordance with embodiments of the present invention.
Figure 3B:
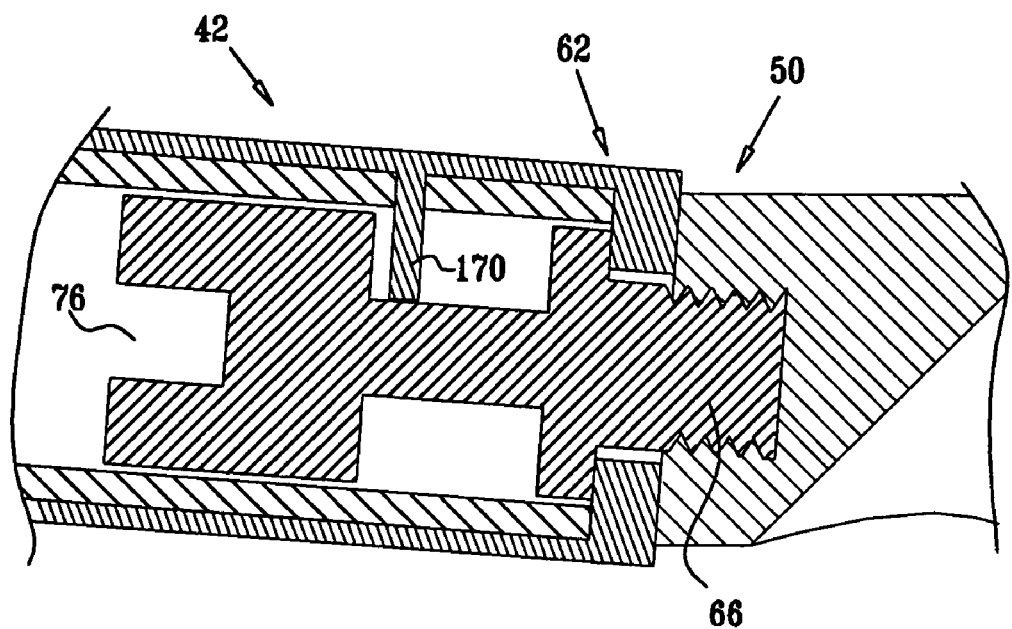

Reference is now made to FIGS. 3A and 3B, which are schematic illustrations of additional configurations of coupling assembly 62, in accordance with embodiments of the present invention. In these embodiments, blocking element 70 comprises a blocking element 170. As shown in both FIGS. 3A and 3B, blocking element 170 is shaped as a small protrusion on an inner aspect of coupling assembly 62. For some applications, as shown in FIG. 3B, coupling element 66 is configured such that a portion thereof that includes engagement surface 76 is proximal to blocking element 170.

Reference is now made to FIG. 4, which is a schematic illustration of a detent comprising a snap-like coupling element 200, in accordance with an embodiment of the present invention. In this embodiment, coupling element 66 comprises snap-like coupling element 200. Coupling surface 74 of coupling element 200 comprises one or more movable engagement elements 210, such as spring-loaded ball bearings. An inner surface of proximal end 50 of bone fixation device 48 is shaped so as to define one or more indentations 212, corresponding to engagement elements 210. Indentations 212 are adapted to receive engagement elements 210, in order to couple coupling element 200 to proximal end 50. Activator tool 80 is used to apply pressure to and rotate snap-like coupling element 200 in order to engage engagement elements 210 with indentations 212, and to disengage the engagement elements from the indentations.

Reference is again made to FIG. 2. Coupling element 66 typically comprises a substance having a high strength, such as a metal, in order to strongly couple coupling portion 42 of targeting device 40 to proximal end 50 of bone fixation device 48. The substance is typically radiopaque. A length L1 from a distal end 84 to a proximal end 86 of coupling element 66 is typically less than about 15 mm, such as less than about 11 mm or less than about 9 mm. Typically, a distance D1 from proximal end 86 of coupling element 66 to a proximal end 88 of bore 72 is greater than about 25 mm, such as greater than about 30 mm, greater than about 35 mm, or greater than about 45 mm, e.g., about 75.3 mm.

Coupling assembly 62 typically further comprises a generally radially symmetrical support element 90, which is shaped so as to define a connection support region 92 and a generally cylindrically-shaped attachment region 94. Support region 92 engages coupling element 66 when the coupling element is tightened. Attachment region 94 attaches support element 90 to coupling portion 42 of targeting device 40. Coupling assembly 62 typically comprises a substance having a high strength, such as a metal.

In an embodiment of the present invention, chamber 64 is shaped so as to define one or more holes 96 extending between (a) inside the chamber, and (b) outside of coupling portion 42 of targeting device 40. For some applications, attachment region 94 is also shaped so as to define holes 96. Holes 96 are typically useful for facilitating cleaning of chamber 64 between uses, such as by flushing chamber 64 with a cleaning solution via holes 96.

In an embodiment, a longitudinal axis of coupling portion 42 of targeting device 40 diverges by an angle alpha from a longitudinal axis of bone fixation device 48. For some applications, alpha is between about 2 and about 6 degrees (e.g., 4 degrees), or greater than 6 degrees, e.g., 10 degrees.

Figure 5:
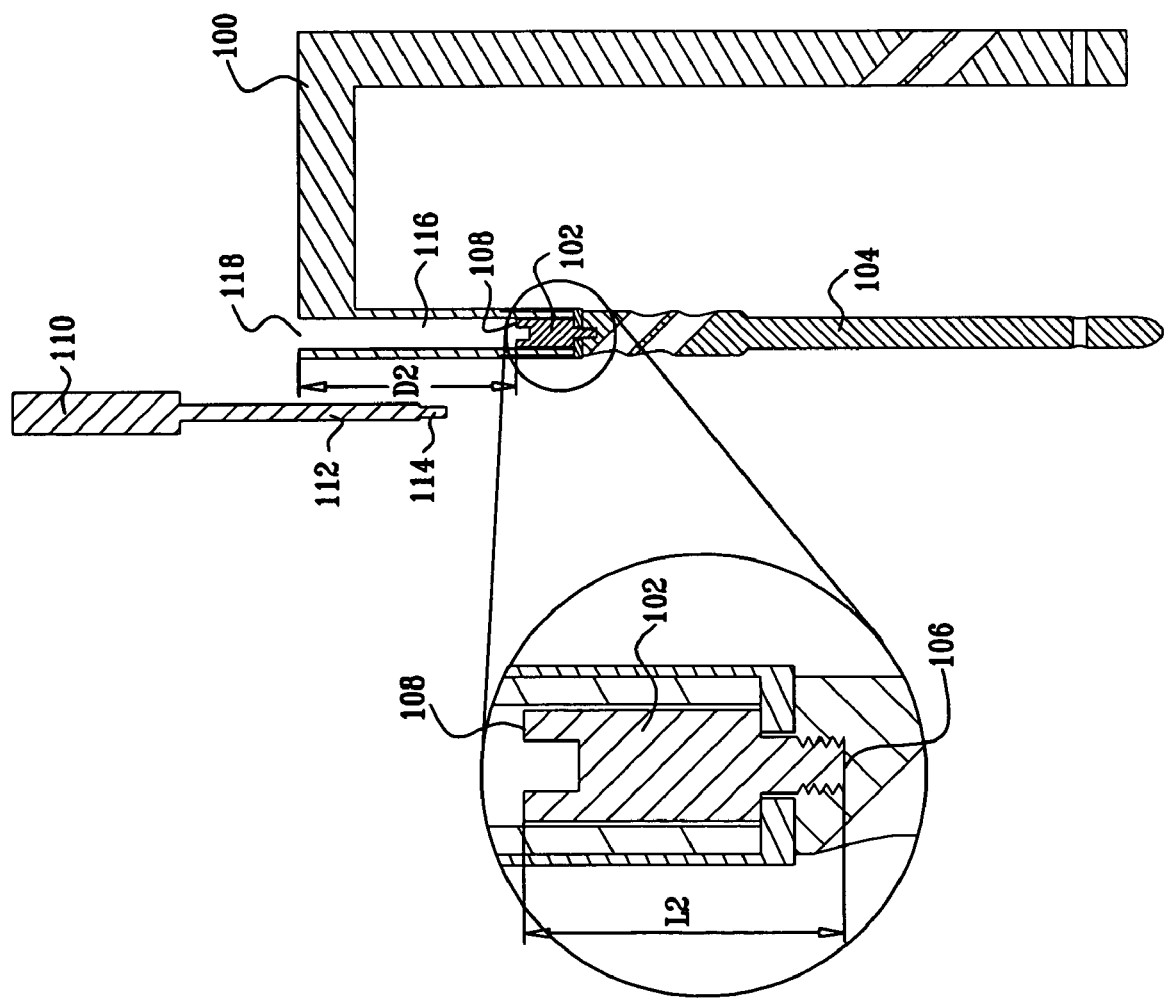
FIG. 5 is a schematic illustration of another targeting device, in accordance with an embodiment of the present invention.

Reference is now made to FIG. 5, which is a schematic illustration of a targeting device 100, in accordance with an embodiment of the present invention. Targeting device 100 is generally similar to targeting devices known in the art, such as targeting device 10, described hereinabove with reference to FIG. 1. However, unlike in the prior art devices, a coupling element 102, such as a screw, for attaching targeting device 100 to a bone fixation device 104, such as an IM nail, has a length L2 from a distal end 106 to a proximal end 108 of screw 102 that is less than about 30 mm, such as less than about 15 mm, less than about 11 mm, or less than about 9 mm. A screwdriver 110 having an elongated shaft 112 is provided for tightening and loosening screw 102. For some applications, screw 102 and a distal tip 114 of screwdriver 110 are magnetized, to aid in insertion and removal of screw 102 through an elongated bore 116 of targeting device 100. Alternatively or additionally, distal tip 114 comprises gripping elements to aid in insertion of screw 102. Typically, a distance D2 from proximal end 108 of screw 102 to a proximal end 118 of bore 116 is greater than about 25 mm, such as greater than about 30 mm, greater than about 35 mm, or greater than about 45 mm, when screw 102 couples targeting device 100 to bone fixation device 104.

As appropriate, techniques described herein are practiced in conjunction with methods and apparatus described in U.S. patent application Ser. No. 10/616,218, filed Jul. 8, 2003, entitled, "Intramedullary nail system and method for fixation of a fractured bone," which is incorporated herein by reference.

As appropriate, dimensions of various components described hereinabove are varied in accordance with the dimensions of a bone which is being treated. For example, smaller bones (e.g., phalanges) may be treated with smaller components.

It will be appreciated that although some embodiments of the present invention have been shown and described herein for use in a femur, these embodiments may be adapted for use in other bones of the extremities, such as the tibia and humerus, *mutatis mutandis*. It will also be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a bone fixation device, the apparatus comprising
   a targeting device, adapted to aid in fixation of the bone fixation device to a bone of a subject, the targeting device comprising:
      a coupling element, adapted to couple the targeting device to the bone fixation device; and
      a coupling assembly, adapted to hold the coupling element, and to prevent the coupling element from exiting the coupling assembly in lateral, rearward and forward directions even when the coupling element is not coupled to the bone fixation device,
      the coupling element being prevented from exiting the coupling assembly in the lateral direction by a support element of the coupling assembly and in the forward direction by a support region of the support element,
      the coupling assembly being shaped so as to define a blocking element that prevents the coupling element from exiting the coupling assembly in the rearward direction,
      the blocking element being generally cylindrical in shape, and defining a bore through which access is provided to a proximal end of the coupling element.

2. The apparatus according to claim 1, wherein the targeting device comprises at least one radiolucent material.

3. The apparatus according to claim 1, wherein the bone fixation device includes an intramedullary (IM) nail, and the targeting device is adapted to aid in fixation of the IM nail to the bone.

4. The apparatus according to claim 1, wherein the bone fixation device includes a plate, and the targeting device is adapted to aid in fixation of the plate to the bone.

5. The apparatus according to claim 1, wherein the bone fixation device includes at least one anchoring screw, and the targeting device is shaped so as to define at least one transverse hole therethrough for aiding in aligning the at least one anchoring screw with the bone fixation device.

6. The apparatus according to claim 1, wherein the coupling element comprises a screw.

7. The apparatus according to claim 1, wherein the coupling element comprises metal.

8. The apparatus according to claim 1, wherein the coupling assembly comprises at least one radiopaque material.

9. The apparatus according to claim 1, wherein the targeting device comprises a support element shaped so as to define a support region, which region is adapted to engage the coupling element when the coupling element is coupled to the bone fixation device.

10. The apparatus according to claim 1, wherein the targeting device is shaped to define a longitudinal axis thereof in a portion of the targeting device that couples with the bone fixation device, the bone fixation device is shaped to define a longitudinal axis thereof, and the longitudinal axis of the portion of the targeting device diverges by an angle greater than 2 degrees from the longitudinal axis of the bone fixation device when the coupling element is coupling the targeting device to the bone fixation device.

11. The apparatus according to claim 1, wherein the coupling assembly is shaped so as to define a chamber that is adapted to hold the coupling element.

12. The apparatus according to claim 11, wherein the chamber is shaped so as to define one or more holes extending between the inside the chamber and the outside of the targeting device.

13. The apparatus according to claim 1, wherein the coupling element has a proximal end and a distal end, and a distance between the proximal end and the distal end is less than about 15 mm.

14. The apparatus according to claim 13, wherein the distance is less than about 11 mm.

15. The apparatus according to claim 14, wherein the distance is less than about 9 mm.

16. The apparatus according to claim 1, wherein the coupling element has a proximal coupling element end, the targeting device is shaped so as to define an elongated bore having a distal bore end and, at a proximal bore end thereof, a proximal opening, the coupling assembly is positioned in a vicinity of the distal bore end, and a distance from the proximal coupling element end to the proximal bore end is greater than about 25 mm, when the coupling element couples the targeting device to the bone fixation device.

17. The apparatus according to claim 16, wherein the distance is greater than about 30 mm.

18. The apparatus according to claim 17, wherein the distance is greater than about 35 mm.

19. The apparatus according to claim 18, wherein the distance is greater than about 45 mm.

20. Apparatus for use with a bone fixation device, comprising
    a targeting device for aiding in fixation of the bone fixation device to a bone of a subject, the targeting device comprising:
       an axially extending coupling element for coupling the targeting device to the bone fixation device; and
       a coupling assembly including a chamber in which at least a portion of the coupling element is received,
       the coupling assembly including means for preventing the coupling element from exiting the chamber in a lateral direction and rearward and forward axial directions including when the coupling element is not coupling the targeting device to the bone fixation device,
       the means comprising a blocking element arranged axially rearward of the coupling element to thereby prevent the coupling element from exiting the chamber in the rearward direction,
       the blocking element defining a bore through which a tool is insertable into engagement with the coupling element.

21. The apparatus according to claim 20, wherein the coupling element is movable in the chamber relative to the blocking element.

22. The apparatus according to claim 20, wherein the blocking element is cylindrically shaped.

23. The apparatus according to claim 20, wherein the means further comprise a support element for preventing the coupling element from exiting the chamber in the lateral and forward directions.

24. The apparatus according to claim 23, wherein the support element includes a cylindrical region surrounding the coupling element for preventing the coupling element from exiting the chamber in the lateral direction and a support region for preventing the coupling element from exiting the chamber in the forward direction.

25. The apparatus according to claim 20, wherein the means further comprise a support element for preventing the coupling element from exiting the chamber in the lateral and forward directions.

26. The apparatus according to claim 25, wherein the support element includes a cylindrical region surrounding the coupling element for preventing the coupling element from exiting the chamber in the lateral direction and a support region for preventing the coupling element from exiting the chamber in the forward direction.

27. The apparatus according to claim 20, wherein the coupling element comprises a screw.

28. The apparatus according to claim 20, wherein the targeting device comprises at least one radiolucent material.

29. The apparatus according to claim 20, wherein the bone fixation device includes an intrainedullary (TM) nail, and the targeting device is adapted to aid in fixation of the TM nail to the bone.

* * * * *